(12) United States Patent
Xiao et al.

(10) Patent No.: US 12,220,332 B2
(45) Date of Patent: Feb. 11, 2025

(54) LUMINAL STENT

(71) Applicant: LIFETECH SCIENTIFIC (SHENZHEN) CO., LTD, Shenzhen (CN)

(72) Inventors: Benhao Xiao, Shenzhen (CN); Xuan Wu, Shenzhen (CN)

(73) Assignee: LIFETECH SCIENTIFIC (SHENZHEN) CO., LTD, Shenzhen (CN)

( * ) Notice: Subject to any disclaimer, the term of this patent is extended or adjusted under 35 U.S.C. 154(b) by 0 days.

(21) Appl. No.: 16/954,347

(22) PCT Filed: Dec. 18, 2018

(86) PCT No.: PCT/CN2018/121744
§ 371 (c)(1),
(2) Date: Jun. 16, 2020

(87) PCT Pub. No.: WO2019/128780
PCT Pub. Date: Jul. 4, 2019

(65) Prior Publication Data
US 2021/0093471 A1 Apr. 1, 2021

(30) Foreign Application Priority Data
Dec. 28, 2017 (CN) .......................... 201711461875.1

(51) Int. Cl.
*A61F 2/82* (2013.01)
(52) U.S. Cl.
CPC .......... *A61F 2/82* (2013.01); *A61F 2002/823* (2013.01); *A61F 2220/0025* (2013.01); *A61F 2220/0083* (2013.01)

(58) Field of Classification Search
CPC ........ A61F 2/07; A61F 2/82; A61F 2002/077; A61F 2002/823; A61F 2/844; A61F 2/848; A61F 2/86
See application file for complete search history.

(56) References Cited

U.S. PATENT DOCUMENTS

| | | | | |
|---|---|---|---|---|
| 4,768,507 A | * | 9/1988 | Fischell | A61F 2/88 623/1.11 |
| 6,729,356 B1 | * | 5/2004 | Baker | D03D 3/08 28/142 |

(Continued)

FOREIGN PATENT DOCUMENTS

| | | |
|---|---|---|
| CN | 202875531 U | 4/2013 |
| CN | 104135966 A | 11/2014 |

(Continued)

OTHER PUBLICATIONS

International Search Report issued on Mar. 19, 2019 in corresponding International Application No. PCT/CN2018/121744; 8 pages.

(Continued)

*Primary Examiner* — Christopher D. Prone
(74) *Attorney, Agent, or Firm* — Maier & Maier, PLLC

(57) ABSTRACT

A luminal stent, including a tubular body and a skirt sleeved on the tubular body. One end of the skirt is a fixed end, and the fixed end is sealedly connected to the outer surface of the tubular body; the other end of the skirt is a free end; on a section passing through the central axis of the tubular body, the ratio of the distance between the fixed end and the free end located on the same side of the central axis of the tubular body to the vertical distance between two points of the free end on both sides of the central axis of the tubular body along the radial direction of the skirt is less than 1/2.

15 Claims, 8 Drawing Sheets

(56) References Cited

U.S. PATENT DOCUMENTS

| | | | |
|---|---|---|---|
| 2003/0236567 A1 | 12/2003 | Scimed | |
| 2008/0027481 A1* | 1/2008 | Gilson | A61F 2/86 606/200 |
| 2010/0121424 A1 | 5/2010 | Kubena | |
| 2012/0150274 A1* | 6/2012 | Shalev | A61F 2/958 623/1.12 |
| 2016/0338823 A1* | 11/2016 | Akingba | A61F 2/848 |

FOREIGN PATENT DOCUMENTS

| | | | |
|---|---|---|---|
| CN | 204072390 U | 1/2015 | |
| CN | 105496603 A | 4/2016 | |
| CN | 105662511 A | 6/2016 | |
| WO | WO-2017081679 A1 * | 5/2017 | A61F 2/07 |

OTHER PUBLICATIONS

Extended European Search Report issued on Feb. 8, 2021, in connection with corresponding EP Application No. 18897682.3; 8 pages.

* cited by examiner

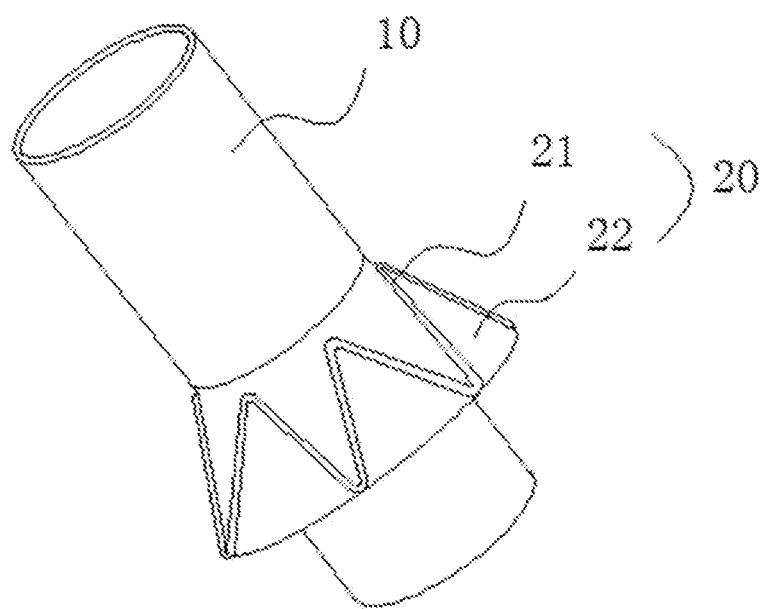
Fig. 1 [PRIOR ART]
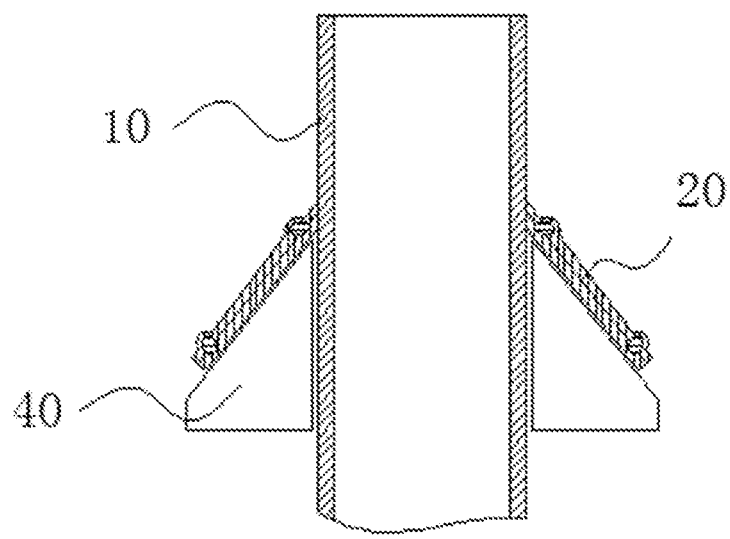
Fig. 2 [PRIOR ART]

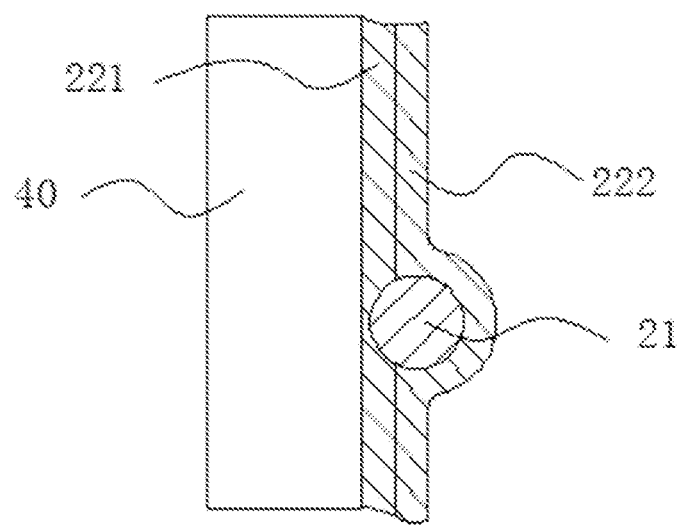
Fig. 3 [PRIOR ART]
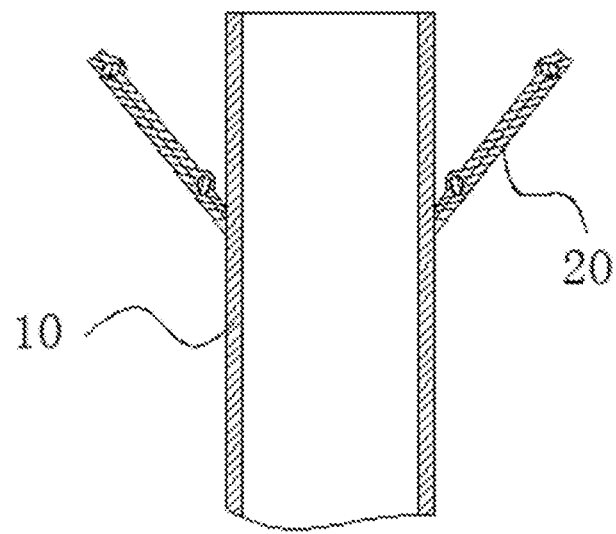
Fig. 4 [PRIOR ART]

LUMINAL STENT

FIELD

The embodiments relate to the field of interventional medical instruments, and in particular, to a luminal stent.

BACKGROUND

For more than ten years, an endovascular aortic repair with aortic membrane-covered stent has been widely used in aneurysms and aortic dissection and other pathologic changes in the thoracic and abdominal aorta, and has become a frontline treatment due to its exact efficacy, less trauma, rapid recovery, and fewer complications. However, for special diseased areas such as the aortic arch, celiac trunk, bilateral renal arteries, or superior mesenteric arteries, the use of the membrane-covered stent may affect the blood supply to the arterial branch vessels. In view of this situation, the membrane-covered stent is usually opened in situ during a surgery by laser or mechanical means, so that the membrane-covered stent produces the expected hole. A branch stent is then transported to the hole to dock with the membrane-covered stent. This treatment protocol overcomes the dependence on the anatomy of branched blood vessels in the human body.

As shown in FIG. 1, a branch stent includes at least a tubular body 10 and a skirt 20 sleeved outside the tubular body 10. The skirt 20 includes a metal rack 21 and an overlay membrane 22 covering the metal rack 21. After the branch stent is implanted into the hole of the membrane-covered stent, the skirt 20 may fill the gap between the tubular body and the hole to prevent internal leakage.

As shown in FIG. 2 and FIG. 3, in the manufacturing process of the skirt of the branch stent, a mold rod 40 is firstly provided outside the tubular body 10. At least one inner membrane 221, a metal rack 21 and at least one layer of the outer mold 222 are then provided in turn on the mode rod 40. After that, the mold ord 40 and the skirt 20 thereon are heat-treated together, so that the inner membrane 221 and the outer mold 222 are fused and bonded to each other under a certain temperature and pressure. Referring to FIG. 3, due to the limitation of the above manufacturing method, the side of the skirt 20 engaged tightly to the mold rod 40 is flat and smooth, while the metal rack 21 protrudes from the side of the skirt 20 distant from the mold rod 40, so that the outer surface of the side of skirt 20 distant from the mold rod 40 is uneven. If the prepared branch stent is directly disposed into the sheathing canal, as the outer surface of the skirt is uneven, it may easily scratch the inner wall of the sheathing canal. It may not only damage the skirt, but also may increase the friction between the skirt and the sheathing canal, leading to increase of the release force, making it difficult for the branch stent to come out of the sheath. Therefore, before disposing the branch stent into the sheathing canal, the skirt needs to be everted. By comparing FIG. 2 and FIG. 4, the side of the skirt engaged tightly to the mold rod then becomes the outer surface of the skirt, which results in a skirt with a flat and smooth outer surface. However, due to the specific structure of the skirt, some skirts cannot be everted, or may only be everted in case the skirt is stretched or bended, which damages the overlay membrane structure of the skirt.

SUMMARY

The embodiments provide a luminal stent that facilitates flanging in view of the defect in the prior art that the skirt may not easily be everted.

A solution adopted by the embodiments to solve this problem is as follows.

A luminal stent is provided, including a tubular body and a skirt sleeved on the tubular body. One end of the skirt is a fixed end, and the fixed end is sealedly connected with the outer surface of the tubular body. The other end of the skirt is a free end. On a section passing through the central axis of the tubular body, the ratio of the distance between the fixed end and the free end located on the same side of the central axis of the tubular body to the vertical distance of the free ends on both sides of the central axis of the tubular body in the radial direction of the skirt is less than 1/2.

In the luminal stent, along the radial direction of the skirt, the ratio of the vertical distance between the free ends on both sides of the central axis of the tubular body to the vertical distance between the fixed ends on both sides of the central axis of the tubular body is greater than or equal to 3/2.

In the luminal stent, an included angle between a connection line between the free end and the fixed end located on the same side of the central axis of the tubular body and the central axis of the tubular body is not less than 30°.

In the luminal stent, the tubular body includes a first radial support structure, and the skirt includes a second radial support structure, where the second radial support structure is rotatably connected with the first radial support structure.

In the luminal stent, the second radial support structure includes at least one waveform ring, the waveform ring includes a plurality of proximal vertices, a plurality of distal vertices, and a support connecting the proximal vertex and the distal vertex adjacent with each other, and the waveform ring is rotatably connected to the first radial support structure at a position of at least one of the proximal vertices.

In the luminal stent, an included angle between the supports connected on both sides of the proximal vertices is larger than an included angle between the supports connected on both sides of the distal vertices.

In the luminal stent, the plurality of proximal vertices include at least one first proximal vertex and a plurality of second proximal vertices, and the waveform ring is rotatably connected to the first radial support structure at the first proximal vertex.

In the luminal stent, the distance between the first proximal vertex and the distal vertex is greater than the distance between the second proximal vertex and the distal vertex.

In the luminal stent, an included angle between the supports connected on both sides of the first proximal vertex is smaller than an included angle between the supports connected on both sides of the second proximal vertex.

In the luminal stent, the distal vertex is located in the same plane perpendicular to the central axis of the skirt.

In the luminal stent, an included angle between the supports connected on both sides of the distal vertex is about 10°-30°.

In the luminal stent the wire diameter of the waveform ring is about 0.05 mm to 0.15 mm.

In the luminal stent, the second radial support structure and the first radial support structure are hooked to each other or connected through a connection ring.

Thus, implementing the luminal stent in the embodiments has at least the following beneficial effects: by adjusting the ratio of the distance between the fixed end and the free end on the same side of the tubular body to the vertical distance between the two fixed ends along the radial direction of the skirt, the skirt may evert without being stretched or bent under the condition of compressing the two fixed ends along the radial direction.

BRIEF DESCRIPTION OF THE DRAWINGS

The embodiments will be further described below with reference to the accompanying drawings, in which:

FIG. 1 is a perspective view of a branch stent in the prior art;

FIG. 2 is the sectional view of branch stent shown in FIG. 1;

FIG. 3 is the structural schematic diagram of the skirt of branch stent shown in FIG. 1;

FIG. 4 is the sectional view after flanging of the skirt of branch stent shown in FIG. 2;

DETAILED DESCRIPTION OF THE EMBODIMENTS

Embodiments will now be described in detail with reference to the accompanying drawings for clearer understanding of the features, objects, and effects.

To facilitate the description, a lumen is described by taking a blood vessel as an example, which may be an aortic arch, or a thoracic aorta, or an abdominal aorta. Persons of ordinary skill in the art may appreciate that the use of a blood vessel for illustration is only for exemplary purpose, and is not a limitation. A solution of the embodiments is applicable to various human lumens, such as the lumen of the alimentary canal, etc. Such improvements and modifications based on the embodiments are all within the scope of the embodiments. In addition, in explaining the blood vessel, the direction may be defined according to the flow direction of blood, and the blood flow is defined as from the proximal end to the distal end. Unless otherwise specified, the radial support structure described refers to a closed waveform ring common in the art arranged along the axial direction of the membrane-covered stent.

Figure 5:
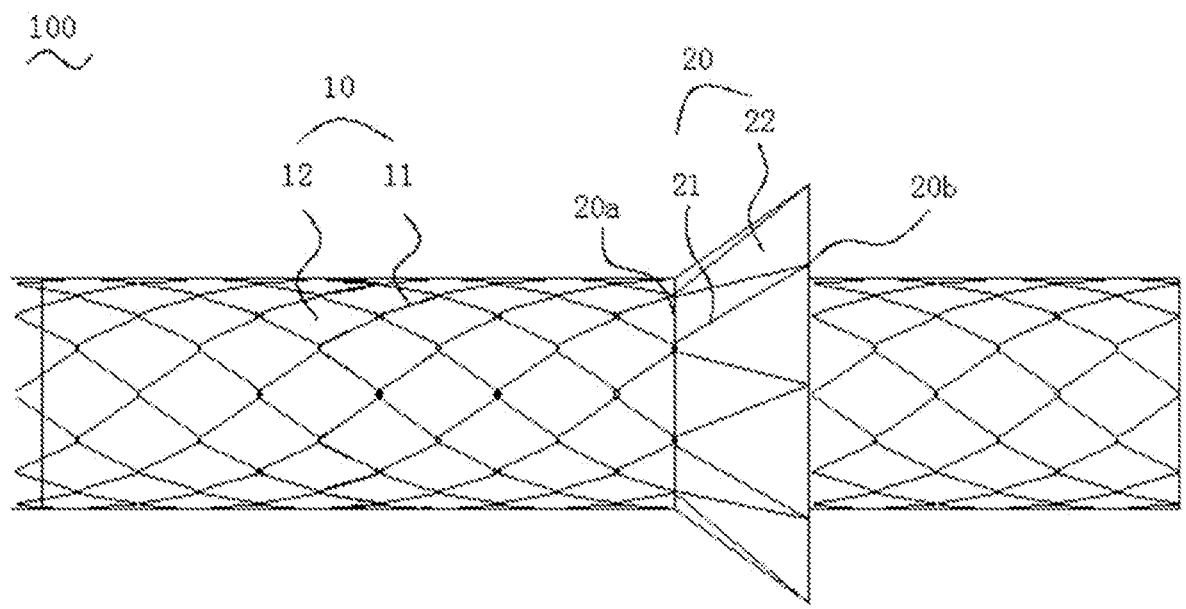
FIG. 5 is a schematic diagram of a luminal stent provided by one of the exemplary embodiments.

As shown in FIG. 5, an exemplary embodiments provides a luminal stent 100, including a tubular body 10 and a skirt 20 sleeved outside the tubular body 10.

The tubular body 10 is a tubular structure with an axial direction, which may serve as a new blood flow channel after being implanted in a blood vessel. The tubular body 10 includes at least a first radial support structure 11 and a first overlay membrane 12 covering the first radial support structure 11. The first radial support structure 11 fits with the first overlay membrane 12 to form the side wall of the tubular body 10.

The first radial support structure 11 may be made of various biocompatible materials, such as nickel-titanium, stainless steel, and the like. The first radial support structure 11 may include a plurality of turns of waveform rings in the axial direction, such as a plurality of turns of Z-shaped waves, M-shaped waves, or other structures that may be radially compressed to a small diameter; or may include a spirally wound structure; or may include a mesh structure. The first radial support structure 11 may be wound from a metal wire or cut from a metal tube. The first overlay membrane 12 is made of a polymer material with good biocompatibility, such as a PET membrane, a PTFE membrane, etc. The first overlay membrane 12 may cover on the first radial support structure 11 by sewing or hot melting.

Through the above-mentioned first radial support structure 11, the tubular body 10 has a radial expansion capability, and may be compressed under an external force and may restore to and maintain its original shape by self-expansion or by mechanical expansion (for example, balloon inflation) after the external force is withdrawn, whereby after the tubular body 10 is implanted into the lumen, it may be fixed in the lumen by engaging against the wall of the lumen by its radial support force. It can be noted that, unless otherwise specified, it is the initial shape of the luminal stent after radial deployment that is described in this embodiment. Through the first overlay membrane 12 described above, the tubular body 10 may isolate a diseased area of a lumen. For example, it may isolate an arterial dissection or an aneurysm after being implanted into an arterial blood vessel.

The skirt 20 includes at least a second radial support structure 21 and a second overlay membrane 22 covering the second radial support structure 21. The second radial support structure 21 and the second overlay membrane 22 of the skirt 20 may be a same or similar radial support structure and overlay membrane as those of the above-mentioned tubular body 10, therefore, they will not be repeated here for the sake of brevity. With the second radial support structure 21, the skirt 20 has radial expansion capability.

One end of the skirt 20 is a fixed end 20a, and the fixed end 20a may be sealedly connected to the outer surface of the tubular body 10 by sewing or hot melting. For example, the second overlay membrane 22 of the fixed end 20a may be thermally fused with the first overlay membrane 11 of the tubular body 10 together to achieve the sealed connection. The other end of the skirt 20 is a free end 20b, and the free end 20b is radiated outwards, so that the skirt 20 forms an approximately conical structure, that is, the cross section of the skirt 20 gradually increases along the direction from the fixed end 20a to the free end 20b.

Figure 6:
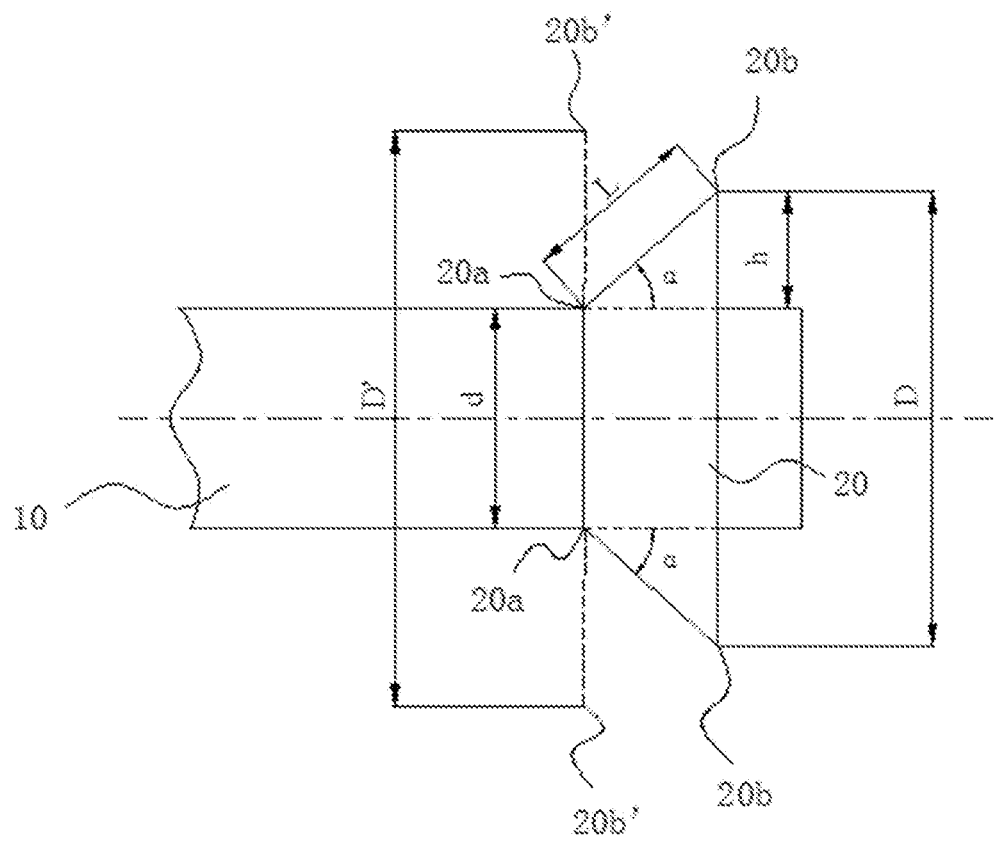
FIG. 6 is a schematic diagram of flanging of the luminal stent shown in FIG. 5 when the vertical distance of the two fixed ends along the radial direction of the skirt on the section passing through the central axis of the skirt is kept unchanged.

Referring to FIG. 6, in a section passing through the central axis of the tubular body 10, the ratio of the distance L between the fixed end 20a and the free end 20b on the same side of the central axis of the tubular body 10 to the vertical distance D between the two free ends 20b along the radial direction of the skirt 20 is less than 1/2.

During the eversion of the skirt 20, the free end 20b turns around the fixed end 20a on the same side in a direction away from the tubular body 10, and the vertical distance h from the free end 20b to the outer surface of the tubular body 10 increases continuously. When the line connecting the free end 20b with the fixed end 20a on the same side is perpendicular to the central axis of the luminal stent, as shown by the dotted line in FIG. 6, the vertical distance between the free end 20b' and the outer surface of the tubular body 10 reaches the maximum. At this time, the vertical distance between the two free ends 20b' in the radial direction of the skirt 20 is D'. It may be appreciated that, because the second radial support structure 21 and the second overlay membrane 22 are not ductile, the skirt 20 will not be elastically deformed. In case the vertical distance d between the two fixed ends 20a along the radial direction of the skirt 20 is constant, it is necessary to stretch the skirt 20 to gradually increase D to D', or bend the skirt 20 so that the vertical distance h from the free end 20b to the outer surface of the tubular body 10 does not increase, but stretching or bending the skirt 20 will damage the overlay membrane structure of the skirt 20, leading to irreversible damage to the skirt 20.

Figure 7:
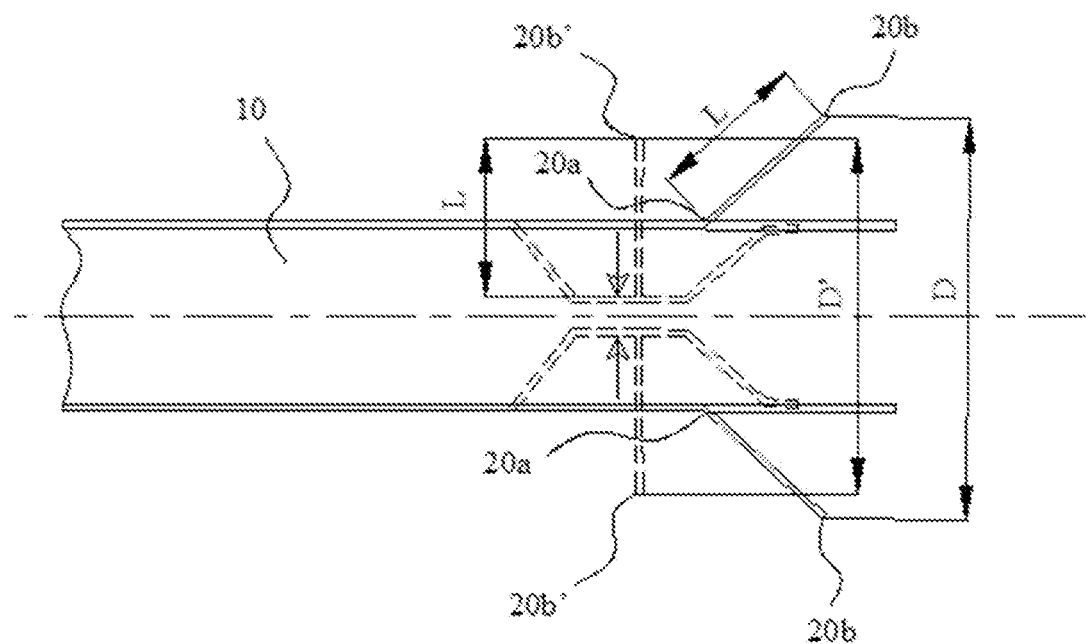
FIG. 7 is a schematic view of flanging of the luminal stent shown in FIG. 5 after compressing the two fixed ends in the radial direction in a section passing through the central axis of the skirt.

Referring also to FIG. 7, when the distance L between the fixed end 20a and the free end 20b on the same side of the tubular body 10 is less than D/2, the two fixed ends 20a may be compressed radially so that D' is not greater than D, that is, flanging without stretching or bending the skirt 20. The direction shown by the arrow in FIG. 7 is the direction in which the two fixed ends 20a are compressed radially. The dotted line shows the schematic diagram of the luminal stent when the line connecting the free end 20b and the fixed end 20a on the same side is perpendicular to the central axis of the luminal stent after the two fixed ends 20a are compressed radially.

It may be seen from the above that by adjusting the ratio of L and D, the skirt 20 may evert without being stretched or bent when the two fixed ends 20a are compressed radially.

Furthermore, the ratio of the vertical distance D between the two free ends 20b in the radial direction of the skirt 20 to the vertical distance d between the two fixed ends 20a in the radial direction of the skirt 20 is greater than or equal to 3/2. It can be noted that the vertical distance D between the two free ends 20b in the radial direction of the skirt 20 and the vertical distance d between the two fixed ends 20a in the radial direction of the skirt 20 are based on the initial shape after the radial expansion of the luminal stent.

Since the skirt 20 is mainly used to fill the gap between the tubular body 10 and the hole of the membrane-covered stent to prevent internal leakage, if the ratio of the vertical distance D between the two free ends 20b along the radial direction of the skirt 20 to the vertical distance d between the two fixed ends 20a along the radial direction of the skirt 20 is too small, the skirt 20 may fail to completely fill the gap, leading to type III internal leakage.

In the manufacturing process of the skirt 20, a mold rod is required to be sheathed on the tubular body 10. If the included angle α between the connection line of the fixed end 20a and the free end 20b on the same side of the tubular body 10 and the center axis of the skirt 20 is too small, the included angle of the corresponding mold rod is also small, and the mold rod with a small included angle may not be easy to process. Therefore, to facilitate the processing, the included angle α between the connection line of the free end 20b and the fixed end 20a on the same side of the tubular body 10 and the center axis of the skirt 20 is not less than 30°. It may be appreciated that, in a section passing through the central axis of the skirt 20, the included angle α on both sides of the tubular body 10 may be the same or different.

Figure 8:
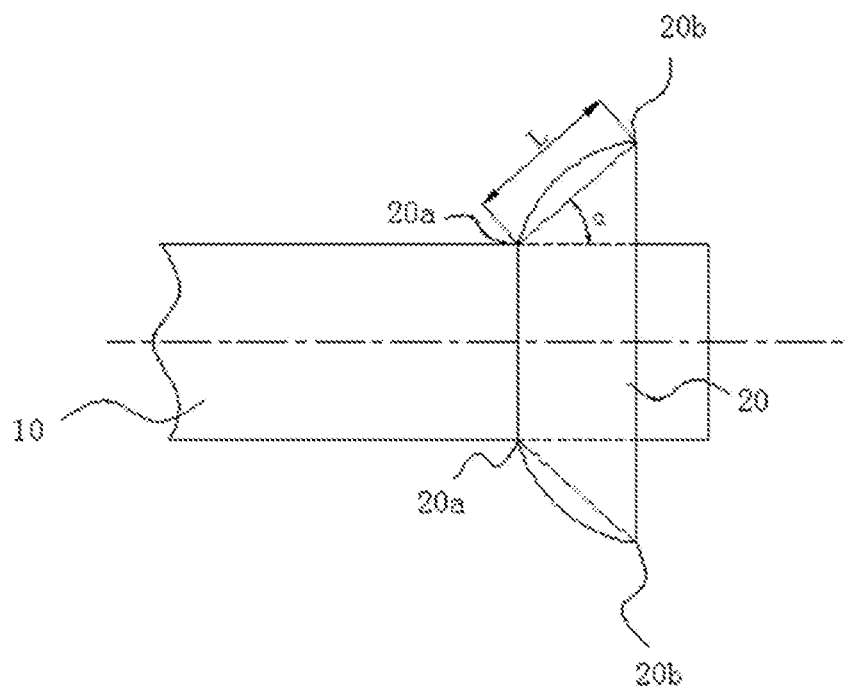
FIG. 8 is a schematic view of the luminal stent shown in FIG. 5 where, in a cross section passing through the central axis of the skirt, the contour line of the skirt is arc-shaped.
Figure 9:
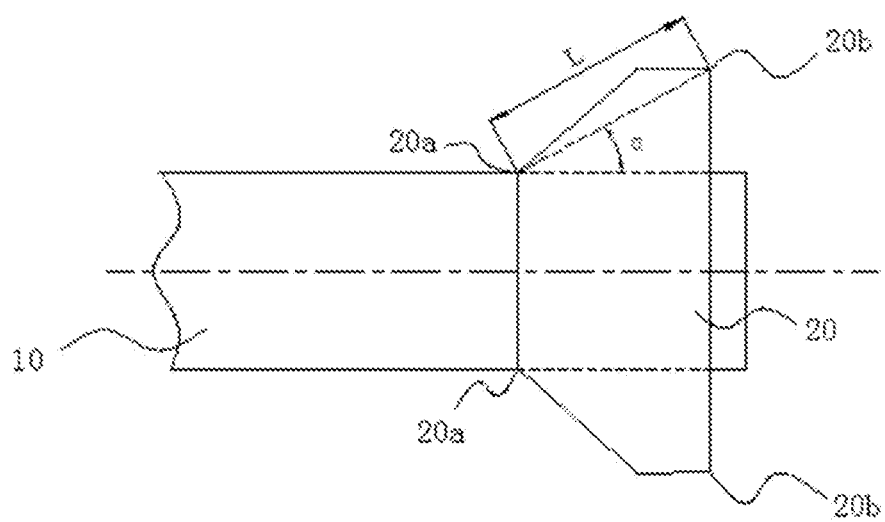
FIG. 9 is a schematic view of the luminal stent shown in FIG. 5 where, in a section passing through the central axis of the skirt, the contour line of the skirt is a mixed line segment connected by straight lines.

In this embodiment, the tubular body 10 is shaped as a straight tube, and the skirt 20 is shaped as a frustum. In a section passing through the central axis of the skirt 20, the contour line of the skirt 20 is a straight line, and the vertical distance d between the two fixed ends 20a along the radial direction of the skirt 20 is the outer diameter of the tubular body 10. It may be appreciated that, in other embodiments, in a section passing through the central axis of the skirt 20, the contour line of the skirt 20 may also be an arc, a mixed line segment of a straight line and a straight line, a combined line segment of a straight line and an arc, or other irregular line segments. As shown in FIG. 8, in a section passing through the central axis of the skirt 20, the contour line of the skirt 20 is arc-shaped. Alternatively, as shown in FIG. 9, in a section passing through the central axis of the skirt 20, the contour line of the skirt 20 is a mixed line segment of a straight line and a straight line.

Figure 10:
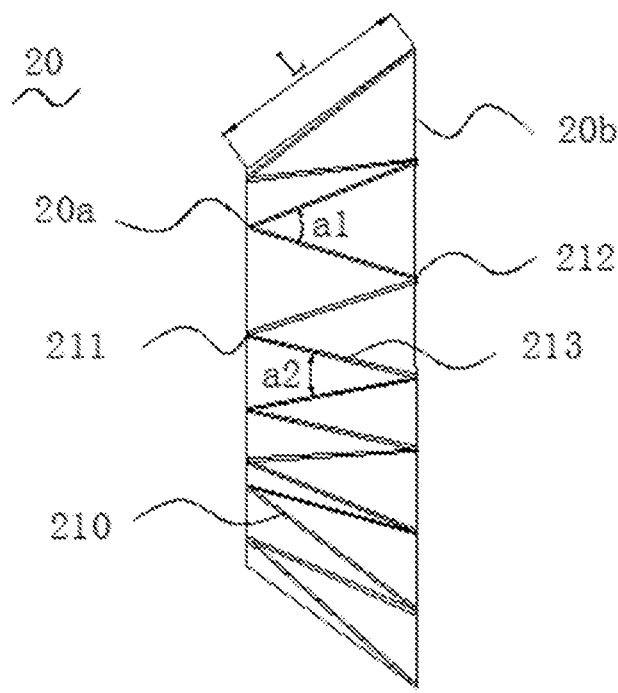
FIG. 10 is a schematic structural diagram of the skirt of the luminal stent shown in FIG. 5.

As shown in FIG. 10, the second radial support structure 21 includes at least one waveform ring 210, and each waveform ring 210 is a closed ring-shaped structure including a plurality of proximal vertices 211, a plurality of distal vertices 212, and a support 213 connecting the adjacent proximal vertex 211 and the distal vertex 212, and the proximal vertices 211 and the distal vertices 213 correspond to the peaks or troughs of the waveform, respectively. In this embodiment, the second radial support structure 21 includes one waveform ring 210. The plurality of proximal vertices 211 of the waveform ring 210 are located in the same plane perpendicular to the central line of the skirt 20. The plurality of distal vertices 212 are also located in the same plane perpendicular to the central axis of the skirt 20. It may be appreciated that, in other embodiments, the second radial support structure 21 may further include a plurality of waveform rings 210. The plurality of waveform rings 210 are sequentially arranged along the axial direction of the skirt 20, preferably arranged in parallel intervals, or the a plurality of waveform rings 210 are connected to form a mesh structure.

The second radial support structure 21 may be distributed on a part of the skirt 20, that is, along the center axis direction of the skirt 20, and the maximum length of the two ends of the second radial support structure 21 is shorter than the length of the skirt 20. The second radial support structure 21 may also be distributed over the entire skirt 20, that is, along the center axis direction of the skirt 20, and the maximum length of the two ends of the second radial support structure 21 is equal to the length of the skirt 20. In this embodiment, the second radial support structure 21 is distributed over the entire skirt 20. The end of the second radial support structure 21 close to the free end 20b is flush with the free end 20b of the skirt 20. The end of the second radial support structure 21 close to the fixed end 20a is flush with the fixed end 10a of the skirt 20.

Figure 11:
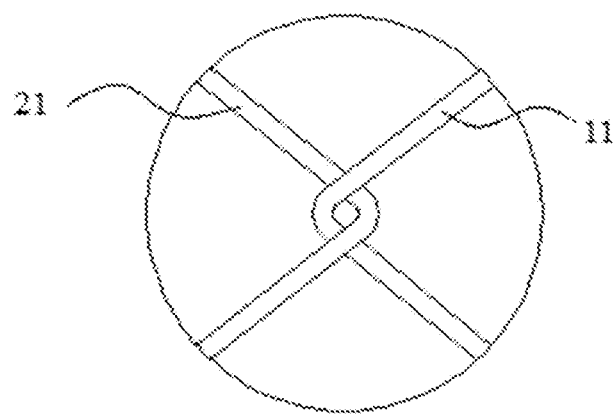
FIG. 11 is a schematic view of the luminal stent shown in FIG. 5 with a second radial support structure and a first radial support structure being hooked with each other.
Figure 12:
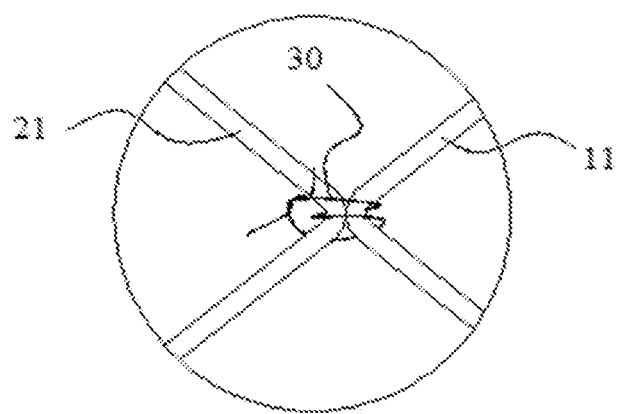
FIG. 12 is a schematic diagram of the luminal stent shown in FIG. 5 with a second radial support structure and a first radial support structure being connected through a connection ring.

Additionally, the end of the second radial support structure 21 close to the fixed end 20a is rotatably connected to the first radial support structure 11 of the tubular body 10. Due to the poor mechanical behavior of the overlay membrane, if the skirt 20 and the tubular body 10 are connected only by the overlay membrane, the skirt 10 is easily pulled or deformed when flanging. It may increase the connection strength between the skirt 20 and the tubular body 10 by connecting the second radial support structure 21 to the first radial support structure 11, which in turn avoids the skirt 10 from being deformed or broken during the flanging, and also facilitates the eversion of the skirt. It may be appreciated that the embodiments do not limit the manner of the rotatable connection between the second radial support structure 21 and the first radial support structure 11. As shown in FIG. 11, at least one wave peak (or wave trough) of the second radial support structure 21 and at least one wave trough or (wave peak) of the first radial support structure 11 are hooked to each other. Alternatively, as shown in FIG. 12, at least one wave peak (or wave trough) of the second radial support structure 21 and at least one wave trough or (wave peak) of the first radial support structure 11 are connected through a connection ring 30, which may be formed by winding with a flexible wire, or a metal ring made of a biocompatible material, such as nickel titanium, stainless steel and other materials. In this embodiment, all the peaks (or troughs) of the side of the second radial support structure 21 close to the fixed end 20a are connected to the first radial support structure 11. It may be appreciated that, in other embodiments, a part of the peaks (or troughs) of the side of the second radial support structure 21 close to the fixed end 20a may be connected to the first radial support structure 11.

Figure 13:
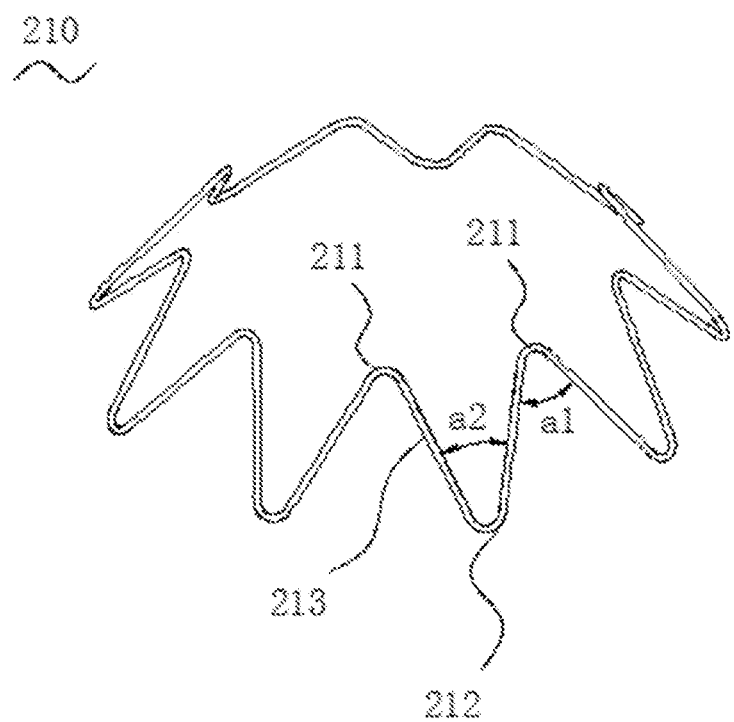
FIG. 13 is a schematic structural diagram of a second radial support structure of the skirt shown in FIG. 10.

With reference to FIGS. 10 and 13, the waveform ring 210 is approximately a frustum structure, and the waveform included angle a1 of the side of the waveform ring 210 close to the fixed end 20a is greater than the waveform included angle a2 of the side of the waveform ring 210 distant from the fixed end 20a. That is, the waveform angle a1 corresponding to the proximal vertex 211 is greater than the waveform angle a2 corresponding to the distal vertex 212. The waveform included angle refers to the included angle between the supports 104 connected on both sides of the same proximal vertex 102 or distal vertex 103.

Figure 14:
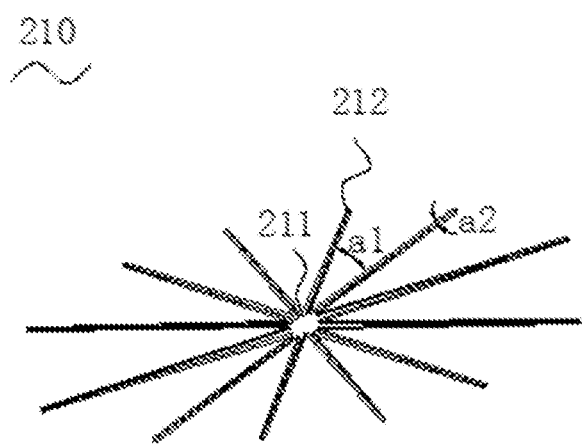
FIG. 14 is a schematic structural diagram of a second radial support structure shown in FIG. 13 after the skirt is compressed in the radial direction.

It may be appreciated that the greater the waveform included angle of the waveform ring 210, the greater the radial force required to squeeze the waveform ring 210, and the waveform ring 210 is prone to plastic deformation or rupture during the extrusion, and if the waveform included angle is too small, it is not conducive to processing. Referring also to FIG. 14, when the fixed end 20a of the skirt 20 is compressed in the radial direction, the plurality of proximal vertices 211 of the waveform ring 210 converge toward one side of the central axis of the skirt 20. The waveform included angle a2 corresponding to the distal vertex 212 of the waveform ring 210 gradually decreases, and tends to 0°. In order to facilitate the compression of the fixed end 20a of the skirt 20 in the radial direction, the waveform included angle a2 corresponding to the distal vertex 212 of the waveform ring 210 is about 10°-30°.

It may also be appreciated that if the wire diameter of the waveform ring 210 is too small, it will affect the radial support force of the second radial support structure 21, but the greater the wire diameter of the waveform ring 210, the greater the radial force required for compressing the waveform ring 210, and the waveform ring 210 is prone to plastic deformation or fracture during the extrusion process. Therefore, the wire diameter of the waveform ring 210 is in a range of 0.05 mm to 0.15 mm, and e.g. ranging from 0.07 mm to 0.13 mm.

Figure 15:
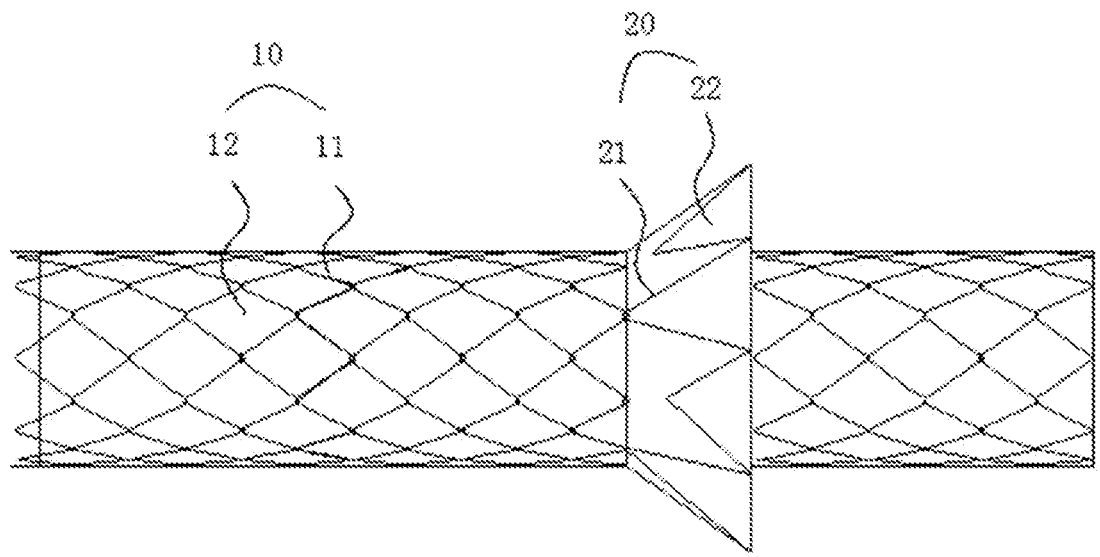
FIG. 15 is a schematic diagram of a luminal stent provided by another of the exemplary embodiments.
Figure 16:
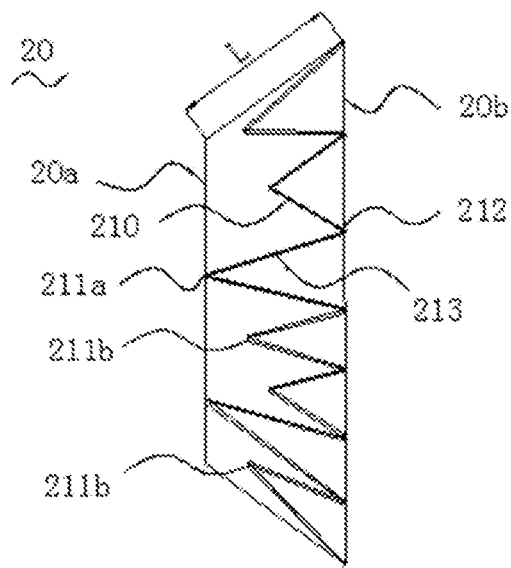
FIG. 16 is a schematic structural diagram of the skirt of the luminal stent shown in FIG. 15.

As shown in FIGS. 15 to 16, a second exemplary embodiment provides a luminal stent, which is different from the first embodiment in the structure of the second radial support structure 21.

As shown in FIG. 16, the second radial support structure 21 includes a waveform ring 210 rotatably connected to the first radial support structure 11. For example, the waveform ring 210 is a closed ring structure, which includes at least one first proximal vertex 211a, a plurality of second proximal vertices 211b, a plurality of distal vertices 212, and a support 213 connecting the adjacent first proximal vertex 211a and the distal vertex 212 or the adjacent second proximal vertex 211b and the distal vertex 212. The first proximal vertex 211a and the second proximal vertex 211b correspond to the peaks of the waveform, and the distal vertices 212 correspond to the troughs of the waveform.

The first proximal vertex 211a extends to the fixed end 10a of the skirt 20 and is rotatably connected to the first radial support structure 11. By taking any one of the plurality of distal vertices 212 as the reference distal vertex, and in the direction of the central axis of the skirt 20, the distance between the first proximal vertex 211a and the reference distal vertex is greater than the distance between the second proximal vertex 211b and the reference distal vertex, and the included angle connected between the supports 104 to both sides of the first proximal vertex 211a is smaller than the included angle between the supports 104 connected to both sides of the second proximal vertex 211b.

It may be appreciated that when the wave height of the waveform ring 210 is constant, the greater the waveform included angle is, the greater the radial support force of the waveform ring 210 is, but if the waveform included angle is too large, it is not conducive to sheathing. Similarly, when the included angle of the wave ring 210 is constant, the smaller the wave height is, the larger the radial support force corresponding to the wave ring 210 is, but if the wave height is too small, it is not possible to maintain the roundness of the skirt 20, hindering the sealing effect of the skirt 20. Therefore, an embodiment may increase the radial support force of the skirt 20 by providing a plurality of second proximal vertices 211b with relatively small wave heights and relatively large waveform included angles, while increasing the connection strength between the skirt 10 and the tubular body 20 by connecting the first proximal vertex 211a and the first support structure 11. For example, the ratio of the distance between the first proximal vertex 211a and the reference distal vertex to the distance between the second proximal vertex 211b and the reference distal vertex is 0.3 to 0.8, and the included angle between supports 213 on both sides of the second proximal vertex 211b is 30° to 150°.

In this embodiment, the a plurality of distal vertices 212 of the waveform ring 210 are located in the same plane perpendicular to the central axis of the skirt 20 and are flush with the free end 20b of the skirt 20, and the first proximal vertex 211a extends to the fixed end 10a of the skirt 20, and is rotatably connected to the first radial support structure 11.

It may be appreciated that the embodiments do not limit the number of the first proximal vertex 211a, and the first proximal vertex 211a may include one or more vertices. When the first proximal vertex 211a includes a plurality of vertices, the plurality of the first proximal vertices 211a are uniformly distributed along the circumferential direction of the skirt 21. For example, the number of the first proximal vertices 211a is less than or equal to the number of the second proximal vertices 211b to increase the radial support force of the skirt 20.

It may also be appreciated that, in other embodiments, the second radial support structure 21 may further include other waveform ring structures, spirally wound structures or mesh structures.

The various features of the above-mentioned embodiments may be combined in any way, and in order to simplify the description, not all possible combinations of the features of the above-mentioned embodiments are described. However, as long as there is no conflict between these features, they should be considered to be within the scope of the description.

The embodiments described above represent only a few embodiments of the present disclosure, but should not be construed to limit the scope of the present disclosure. It should be noted that several variations and modifications may be made by persons of ordinary skill in the art without departing from the spirit of the present disclosure.

The invention claimed is:

1. A luminal stent, comprising:
a tubular body and a skirt sleeved on the tubular body, one end of the skirt is a fixed end sealedly connected with an outer surface of the tubular body, another end of the skirt is a free end, the free end of the skirt is radiated outwards, so that diameters of cross section of the skirt gradually increase along a central axis of the tubular body and along a direction from the fixed end to the free end,
wherein connection points between the fixed end and the outer surface of the tubular body define a first continuous ring, and outermost points of the free end define a second continuous ring,
wherein in a cross-sectional plane passing through the central axis of the tubular body, a distance between a first connection point of the fixed end on the first continuous ring and on the cross-sectional plane and a first outermost point of the free end on the second continuous ring and on the cross-sectional plane is defined as a first distance, the ratio of the first distance to a diameter of the second continuous ring is less than 1/2 when the luminal stent is in an unstressed configuration;
wherein the tubular body comprises a first radial support structure, the skirt comprises a second radial support structure, and the second radial support structure is pivotally connected to the first radial support structure through a connection ring which is formed by winding a flexible wire or a metal ring, or by hooking the first radial support structure with the second radial support structure;
wherein the second radial support structure comprises at least one waveform ring having a plurality of proximal vertices, a plurality of distal vertices and a plurality of supports connecting the adjacent proximal vertex and the distal vertex, the at least one waveform ring is pivotally connected with the first radial support structure at a position of at least one of the proximal vertices; and
wherein an included angle between supports connected on both sides of the proximal vertices of the second radial support structure is greater than an included angle of the supports connected on both sides of the distal vertices of the second radial support structure.

2. The luminal stent according to claim 1, wherein, in the cross-sectional plane passing through the central axis of the tubular body, the ratio of the diameter of the second continuous ring to a diameter of the first continuous ring is greater than or equal to 3/2 when the luminal stent is in the unstressed configuration.

3. The luminal stent according to claim 1, wherein, in the cross-sectional plane passing through the central axis of the tubular body, an included angle formed by a clockwise or counterclockwise rotation of a line segment connecting the first connection point of the fixed end and the first outmost point of the free end relative to the central axis of the tubular body is not less than 30 degrees.

4. The luminal stent according to claim 1, wherein the plurality of proximal vertices of the second radial support structure comprises at least one first proximal vertex and a plurality of second proximal vertices, and the waveform ring of the second radial support structure is rotatably connected with the first radial support structure at the first proximal vertex.

5. The luminal stent according to claim 4, wherein a distance between the first proximal vertex and the distal vertex of the second radial support structure is greater than a distance between the second proximal vertex and the distal vertex of the second radial support structure.

6. The luminal stent according to claim 5, wherein, selecting any one of the plurality of distal vertices of the second radial support structure as a reference distal vertex, a ratio of a distance between the first proximal vertex and the reference distal vertex of the second radial support structure to a distance between the second proximal vertex and the reference distal vertex of the second radial support structure is 0.3 to 0.8, and an included angle between supports on both sides of the second proximal vertex of the second radial support structure is 30° to 150°.

7. The luminal stent according to claim 5, wherein the plurality of distal vertices of the waveform ring of the second radial support structure are located in a same plane perpendicular to the central axis of the skirt and are flush with the free end of the skirt, and the first proximal vertex of the second radial support structure extends to the fixed end of the skirt and is rotatably connected to the first radial support structure.

8. The luminal stent according to claim 5, wherein the number of the first proximal vertices of the second radial support structure is less than or equal to the number of the second proximal vertices of the second radial support structure to increase a radial support force of the skirt.

9. The luminal stent according to claim 5, wherein the second radial support structure further includes other waveform ring structures, spirally wound structures, or mesh structures.

10. The luminal stent according to claim 4, wherein an included angle between the supports connected on both sides of the first proximal vertex of the second radial support structure is smaller than an included angle of the supports connected on both sides of the second proximal vertex of the second radial support structure.

11. The luminal stent according to claim 1, wherein the distal vertices of the second radial support structure are located in a same plane perpendicular to the central axis of the skirt.

12. The luminal stent according to claim 1, wherein the included angle between the supports connected on both sides of the distal vertices of the second radial support structure is 10 degrees to 30 degrees.

13. The luminal stent according to claim 1, wherein a wire diameter of the waveform ring of the second radial support structure is 0.05 mm to 0.15 mm.

14. The luminal stent according to claim 1, where in a cross-sectional plane passing through a central axis of the skirt, an outer contour line of the skirt consists of line segments of straight lines.

15. The luminal stent according to claim 1, wherein along the center axis direction of the skirt, a maximum length of two ends of the second radial support structure is shorter than a length of the skirt, or, along the center axis direction of the skirt, the maximum length of the two ends of the second radial support structure is equal to a length of the skirt.

\* \* \* \* \*